United States Patent
Grose

(10) Patent No.: US 7,029,708 B2
(45) Date of Patent: *Apr. 18, 2006

(54) HERBAL SUPPLEMENT FOR COGNITIVE RELATED IMPAIRMENT DUE TO ESTROGEN LOSS

(75) Inventor: Tricia Grose, Napa, CA (US)

(73) Assignee: Herbaceuticals Inc., Napa, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 10/339,944

(22) Filed: Jan. 10, 2003

(65) Prior Publication Data

US 2003/0228380 A1    Dec. 11, 2003

Related U.S. Application Data

(60) Continuation of application No. 10/139,046, filed on May 2, 2002, now abandoned, which is a division of application No. 09/771,034, filed on Jan. 26, 2001, now Pat. No. 6,426,097.

(60) Provisional application No. 60/178,759, filed on Jan. 28, 2000.

(51) Int. Cl.
*A61K 35/78* (2006.01)

(52) U.S. Cl. .................................................. 424/725
(58) Field of Classification Search ............. 424/195.1, 424/725

See application file for complete search history.

(56) References Cited

U.S. PATENT DOCUMENTS 6,159,476 A * 12/2000 Djananov et al. ............ 424/725
2001/0046522 A1 * 11/2001 Grose .......................... 424/725

FOREIGN PATENT DOCUMENTS

WO    WO 01/54697 A1 * 8/2001

OTHER PUBLICATIONS

Revilla et al. Comparison of Several Procedures Used for the Extraction of Anthocyanins From Red Grapes; J. Agric. Food Chem. 1998, vol. 46, pp. 4592-4597.*

* cited by examiner

*Primary Examiner*—Patricia Leith
(74) *Attorney, Agent, or Firm*—Darby & Darby

(57) ABSTRACT

Estrogen-deficiency related cognitive dysfunction may be improved by administering a composition comprising an herbal composition to a woman. In a preferred embodiment the herbal composition comprises whole plant extract of *Leucojum aestivum*.

6 Claims, No Drawings

HERBAL SUPPLEMENT FOR COGNITIVE RELATED IMPAIRMENT DUE TO ESTROGEN LOSS

This is a continuation of application Ser. No. 10/139,046, filed May 2, 2002, now abandoned, which is a division of application Ser. No. 09/771,034 filed Jan. 26, 2001. now U.S. Pat. No. 6,426,097, which claims priority of provisional application Ser. No. 60/178,759 filed Jan. 28, 2000. Each of these prior applications is hereby incorporated herein by reference, in its entirety.

FIELD OF THE INVENTION

The present invention relates to a method of enhancing memory function and neuronal activity in a woman with estrogen-deficiency by administering an herbal dietary supplement comprising a plant extract of *Leucojum aestivum*.

BACKGROUND OF THE INVENTION

Menopause is a condition in women wherein their bodies no longer produce estrogen and is responsible for physical and physiological changes in the body including bone loss, osteoporosis, cardiovascular disease, senile dementia/ Alzheimer's disease, flushing (hot flashes), urogenital atrophy, dysmenorrhea and acne. Decreased production of estrogen, whether from normal onset of menopause or surgically induced menopause through the removal of the ovaries, is also associated with impaired cognitive function, particularly memory and attention loss, and neurodegeneration.

Estrogen loss has also been correlated with decreased acetylcholine uptake (Simpkins J. W. et al., Neurobiology of Aging, 1994, 15 Suppl. 2, 5195-5197). Acetylcholine is a neurotransmitter found in cholinergic synapses in neuromuscular junctions and in the central nervous system.

In the nervous system, a nerve impulse is transmitted as an electrical signal along a neuron until it reaches the neuron ending. The nerve ending contains vesicles filled with acetylcholine. The nerve impulse stimulates the vesicles to release acetylcholine into the synapse through the pores in the pre-synapse membrane. The acetylcholine diffuses through the synapse gap very quickly (within 1 millisecond) and reaches the post-synapse membrane. The acetylcholine depolarizes the post-synapse membrane, generating an electrical impulse.

The passage of an impulse through the synapse is brief and unidirectional. Once acetylcholine has conveyed the nerve impulse across the synapse, the acetylcholine must be cleared from the gap so that polarization of the post-synaptic membrane can be restored, and the next impulse can be transmitted. Acetylcholinesterase, or simply cholinesterase, found at post-synaptic gaps, hydrolyzes acetylcholine to choline and acetic acid ("acetylcholine uptake"). Estrogen-deficient women, menopausal or post-menopausal, may suffer from increased memory loss and general neurodegeneration due to the effect of low estrogen levels on acetylcholine uptake.

Estrogen-deficient women may also suffer from muscle fatigue. With respect to neuromuscular function, after continuous or repetitive movement or exercise, fatigue reduces the strength and duration of the impulses generated, and the amount of acetylcholine released by the pre-synapse membrane decreases. As a result of these factors, the energy level of the muscle cell is decreased and the excitation threshold becomes more difficult to overcome. Maintenance of motor functions depends on the body's ability to successfully transmit a nerve impulse and stimulate muscle fibers for muscle contraction. A decrease in effective nerve impulse transmissions leads to degeneration of motor function manifested by fatigue and loss in coordination. Although the function of the neuromuscular system is influenced by temporary factors such as stress level and food intake, and long-term factors such as age, genetics, general fitness and nutrition levels, hormone serum levels play a prodigious role in maintaining normal motor function. For example, estrogen deficiency intensifies the effects of impaired neuromuscular connections by further decreasing energy levels of muscle cells due to diminished acetylcholine uptake. The loss of coordination is especially disadvantageous in estrogen-deficient women who may have osteoporosis, as they are more susceptible to the effects of falls, i.e., bone damage.

Acetylcholinesterase inhibitors enhance the effects of acetylcholine, either by inhibiting its hydrolyzation or increasing the time the acetylcholine is present in the synapse. Galanthamine is a known acetylcholinesterase inhibitor. Galanthamine reversibly binds to acetylcholinesterase, inhibiting its action and resulting in an increase in local concentrations of acetylcholine. Galanthamine has been used in the treatment of different diseases of the nervous system such as Alzheimer's disease (U.S. Pat. No. 5,958,903) and Parkinson's disease (U.S. Pat. No. 5,965,571); the treatment of chronic fatigue syndrome (U.S. Pat. No. 5,312,817); as an erectogenic agent in the treatment of male sexual dysfunction (U.S. Pat. No. 5,177,070) as well as the treatment of glaucoma, myasthenia gravis and senile dementia.

Galanthamine is typically used in pharmaceutical compositions in purified form and is obtained by complex chemical extractions from plant sources (U.S. Pat. No. 5,877,172) or chemically synthesized (U.S. Pat. Nos. 5,777,108 and 5,958,903). These processes may be disadvantageous in that they utilize undesirable chemicals such as chlorohydrocarbons and involve purification processes forming galanthamine salts.

A variety of hormone replacement therapies are presently available to help alleviate the deleterious physical and physiological changes associated with menopause. Such regimens include combination therapies using estradiol and conjugated equine estrogens such as Premarin® (Wyeth-Ayerst Laboratories, Princeton, N.J.). Hormone replacement therapies provide benefits in the areas of cardiovascular disease and bone loss, however have numerous side effects including endometrial cancer, increased risk of breast cancer, and vaginal and uterine bleeding. Single agent hormone replacement therapy using the steroidal compound 17 alpha-dihydroequilenin has been disclosed to prevent neurodegeneration associated with cognitive dysfunction in estrogen deficient conditions including menopause (U.S. Pat. No. 5,719,137).

Thus, estrogen replacement therapy is used to treat women with estrogen deficiency to alleviate the deleterious physical and physiological symptoms associated with menopause. However, hormone replacement therapy may not be desirable for treating women who have had cancer or are at a high risk for cancer, especially breast cancer and uterine cancer. Some women for whom hormone replacement therapy is suitable may seek to supplement or enhance these therapies for additional physical or physiological benefits.

Other women may be averse to taking hormone therapies. Therefore, alternative treatments for these women for ameliorating deleterious effects of estrogen loss that are free of the potential risks associated with hormone replacement therapy are highly desirable.

An herbal preparation containing a natural form of an acetylcholinesterase inhibitor which can be used to improve loss in cognitive function in estrogen deficient women has heretofore not been disclosed.

SUMMARY OF THE INVENTION

The present invention provides a method for improving estrogen-deficiency related cognitive dysfunction and neurodegeneration in a woman by administering to the woman an herbal composition comprising a dried whole plant or plant extract. In one embodiment, the dried whole plant or plant extract is from the plant *Leucojum aestivum*.

The applicant has found that a novel herbal composition comprising a powdered form of a whole plant extract comprising galanthamine as an active component provides enhanced memory and attention function in women who have estrogen deficiency. The estrogen deficiency may be menopause related. Menopause may be natural-onset or due to other factor such as surgical removal of the ovaries.

In one embodiment, the composition also comprises a combination of one or more naturally occurring substances such as B vitamins, Co-Q10, ayurvedic herbal extracts, spagyric herbal preparations, nonessential amino acids, antioxidants and minerals which, in combination with the whole plant extract, enhance cognitive function.

In a preferred embodiment, the whole plant extract is of the plant *Leucojum aestivum*. The whole plant extract is present in the herbal composition in an amount of from 0.10–0.6 wt %.

The applicant has also found that the composition of the present invention may improve stamina and endurance in motor function, for example, by prolonging the ability to perform repetitive movement and delaying the onset of muscle fatigue.

DETAILED DESCRIPTION OF THE INVENTION

The present invention concerns novel herbal compositions, a method for their preparation, and a method of using the compositions for improving cognitive dysfunction in women having estrogen-deficiency. At least one of the active ingredients in the composition is most notably a cholinesterase inhibitor.

While the dietary supplement of the present invention may be used by women who wish to supplement their normal dietary regimen to improve their cognitive abilities, the herbal supplement of the invention is particularly beneficial for use by women who are estrogen-deficient and suffer from memory loss or other symptoms of neurodegeneration. The novel herbal supplement of the invention is suitable for use by women who may be undergoing hormone replacement therapy, however is also ideal for estrogen-deficient women for whom hormone replacement therapy is not recommended or not desirable.

The inventor has found that the combination of the whole plant extract of *Leucojum aestivum*, and one or more additional components, including the coenzyme Co-Q 10, Vitamin B and other herbal extracts, works synergistically to promote improved cognitive performance. It is believed that at least one of the active ingredients in the whole plant extract, galanthamine, in its capacity as an acetylcholinesterase inhibitor, improves neural function by inhibiting acetylcholine hydrolyzation and maintains effective levels of acetyicholine in the neural synapse for longer periods of time.

The combination of active ingredients in the herbal composition of the invention secures stronger impulses in the nerves, which are typically found to be decreased or inhibited in estrogen-deficient conditions. Each of the constituents of the combined herbal preparation of the invention has an individual tendency to enhance physical well being. However, the combination of *Leucojum aestivum*, coenzyme Co-Q10 plus vitamin Bs (including vitamin $B_{12}$ and vitamin B complex) and other herbal extracts, especially ayurvedic and spagyric herbal extracts, when administered in proper concentration, stimulate memory function.

Regular exercise, good nutrition and appropriate dietary supplementation can lead to an increase in the energy levels, improving muscle cell function, as well as leading to an extended growth and branching out of the capillary network, and optimization of the function of numerous enzyme systems. Applicant has found that dietary supplementation with the herbal composition of the invention can improve these systems, enhancing the ability to overcome muscle fatigue and ability to maintain activity for longer periods of time, particular repetitive motion. The combination of active ingredients in the herbal composition of the invention secures stronger impulses in the nerves, which are typically found to be decreased or inhibited in estrogen-deficient conditions, and when transmitted to the muscles, generate stronger muscle contractions. The ingredients may further stimulate the release of acetylcholine in the neuron endings and increase the sensitivity of the post-synapse membranes and allow for more sustained and effective physical movement, and significantly improve muscle coordination.

Although one of the active ingredients, galanthamine, found in the whole plant extract of *Leucojum aestivum* can be synthesized by known methods, Applicant has found that using the whole plant extract provides beneficial results. It is believed that the additional components contained within the plant cell wall, as well as the beneficial ingredients contained in the composition as described herein, provide an unexpected synergistic effect on improving memory function performance. An added advantage is that herbal-based compositions provide many other beneficial results to a woman's health, including improved cardiac and vascular function. The benefits of the herbal composition of the invention are particularly advantageous for those individuals reluctant to use pharmaceuticals containing synthetic chemicals because of potential side effects of long term use, or where no nonprescription remedy is available.

For purposes of the invention, a process for preparing the whole plant extract *Leucojum aestivum* is described as follows: the mucilage is removed from intact plants, the remaining plant material is pulverized or finely chopped in a blender, the pulverized plant material is steam distilled, incinerated and the ash is triple washed with water. The treated plant material is then combined with the washings and the mucilage to form the whole plant extract. The whole plant extract may be used unfiltered, or may be filtered through a Whatman filter. Alternatively the resulting whole plant extract may be dried to a powder by air drying at room temperature or accelerated drying at 37° C. The whole plant extract is preferably stored in a dark container at room temperature in a moisture-free environment until used.

Additional organic ingredients may be added to provide incidental benefits. The supplement may contain ingredients that improve oxygen metabolism, antioxidants, factors which directly or indirectly are related to radical scavengers and that improve cardiac function. These include flavonoids, which are widely distributed in the plant kingdom, and are present in plants such as Gingko biloba, Passiflora, incarnata, Matricaria chamomilla, and Tea sinensis. Flavonoids are used as anti-inflammatory agents, antihistamines and vasodilators and most importantly are used for their antioxidant activity. Preferred in the present invention is Gingko biloba extract enriched in flavone glycosides, which increase peripheral circulation and provide additional antioxidant properties to protect cell membranes from radical attack.

The composition may further include a combination of other naturally occurring substances to promote overall wellness and maintain balanced health. Such substances include enzymes such as coenzyme Q10 (CoQ10) chemically known as 2,3-dimethoxy-5-methyl-6-decaprenyl-1,4-benzo- quinone, a fat soluble quinone, which is an essential component of the mitochondrial respiratory chain and may be important in producing energy for all the body's activities. Also included are hormones; growth factors; amino acids; trace elements, vitamins and minerals, including zinc, in amounts 100–500% of RDA; extracts of Chinese plants and herbs, spagyric and ayurvedic herbs; and other nonessential nutrients. The composition can further include acetyl L-carnitine, a metabolic cofactor, which promotes neurological recovery from trauma. While any of these constituents taken alone would be insufficient to produce the desired result, in combination with the active ingredients found in the whole plant extract of Leucojum aestivum, such as galanthamine, they work synergistically to produce significant enhancement of cognitive abilities and motor function in estrogen deficient women. The constituents are not toxic in the amounts provided and have no known side-effects.

For the herbal preparation, the composition of the invention comprises the ingredients provided in Table 1.

TABLE 1

| Ingredient | Broad range (wt %) | Preferred range (wt %) |
|---|---|---|
| Leucojum aestivum | 0.10–0.6 | 0.25–0.40 |
| Spagyric ® Gota Kola | 2.0–5.5 | 3.5–5.0 |
| Zinc | 0.5–3.5 | 1.0–2.5 |
| Vitamin B$_{12}$ | 0.001–0.1 | 0.003–0.06 |
| Vitamin B complex | 0.001–0.3 | 0.005–0.2 |
| Bacopa monniera | 15.0–25.0 | 18.0–21.0 |
| Convolulus pluricaulis | 15.0–25.0 | 18.0–21.0 |
| L-carnitine | 20–60 | 35.0–45.0 |
| Co-Q10 | 2.0–5.5 | 3.5–5.0 |
| Gingko biloba | 8.0–12.0 | 9.5–11.5 |

The desired effect is best achieved with a dose comprising the following preferred concentrations:

2.5 mg (0.33 wt %) of the whole plant extract of Leucojum aestivum 30 mg (3.96 wt %) Spagyric® Gota Kola 15 mg (1.98 wt %) Zinc 0.2 mg (0.026 wt %) Vitamin B$_{12}$ 0.1 mg (0.013 wt %) Vitamin B complex 150 mg (19.8 wt %) Bacopa monniera (ayurvedic)

150 mg (19.8 wt %) Convolulus pluricaulis (ayurvedic)

80 mg (10.56 wt %) Gingko Biloba Extract (24% flavone glycosides/6% terpene lactones)

300 mg (39.6 wt %) Acetyl-L-carnitine 30 mg (3.96 wt %) Co-Q10

The herbal extract of the invention may be administered orally. The optimal daily dose of active ingredient, i.e. Leucojum aestivum extract, is from about 2 to 5 mg.

The herbal extract of the invention may be administered for the purposes of the present invention in the form of capsules or caplets, although other conventional oral dosage forms such as tablets may also be used. In preparing capsules or tablets, standard tablet or capsule making techniques may be employed. In the case of the herbal composition of the invention, the preferred dosage form is a capsule. In this manner the free flowing powders of the herbal extracts and other components in the composition of the invention are readily absorbed into the body.

The invention can be better understood by reference to the following Example, which is provided by way of illustration and not by way of limitation.

EXAMPLE

The utilization of the herbal composition of the present invention is shown to be effective through testing for a year or more by administering the composition of the present invention to menopausal women exhibiting symptoms common to an estrogen deficiency condition.

| | |
|---|---|
| Women | Age Range 40–60 years |
| Dosage | 2.5–5.0 mg of Leucojum aestivum extract |
| Length of Treatment | 30 days to 18 months |
| Estrogen deficiency | menopause, ovariectomy |
| Menopausal Symptoms | memory, attention loss |
| Effects | increase in memory |
| Side Effects | none detrimental |
| | increased energy and improved motor function. |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Various patents, patent applications, and publications are cited herein, the disclosures of which are incorporated by reference in their entireties.

What is claimed is:

1. A daily dietary supplement for improving estrogen deficiency related neurodegeneration and cognitive dysfunction in a woman, said supplement comprising an effective amount of Leucojum aestivum plant extract containing galanthamine; an effective amount of Co-Q10; an effective amount of B vitamins; an effective amount of non-essential amino acids; and an effective amount of antioxidants; and further comprising bacopa monniera and Convolulus pluricaulis.

2. The supplement of claim 1, wherein the effective amount of Leucojun aestivum is about 0.10–0.60 wt %.

3. The supplement of claim 1, wherein the effective amount of Leucojun aestivum is about –0.25–0.40 wt %.

4. The supplement of claim 1, wherein the effective amount of Co-Q10 is about 2.0–5.5 wt %.

5. The supplement of claim 1, wherein effective amount of B vitamins is in the amount of about 0.01–0.05 wt %.

6. An herbal composition for improving estrogen-deficiency related neurodegeneration and cognitive dysfunction in a woman comprising about 0.33 wt % of whole plant extract of *Leucojum aestivum* containing galanthamine; about 0.03 wt % Vitamin Bs; about 39.6 wt % acetyl L-carnitine; about 3.96 wt % Co-Q10; about 1.98 wt % zinc, about 10.56 wt % gingko biloba extract; about 19.8% Bacopa monniera and about 19.8% Convoluluspluricaulis.

* * * * *